US011438135B2

(12) United States Patent
Rico et al.

(10) Patent No.: US 11,438,135 B2
(45) Date of Patent: Sep. 6, 2022

(54) CHAOS CODING BASED COMMUNICATIONS FOR MRI COILS

(71) Applicant: KONINKLIJKE PHILIPS N.V., Eindhoven (NL)

(72) Inventors: Rodrigo Calderon Rico, Gainesville, FL (US); Timothy Ortiz, Alachua, FL (US); George Randall Duensing, Gainesville, FL (US)

(73) Assignee: Koninklijke Philips N.V., Eindhoven (NL)

( * ) Notice: Subject to any disclaimer, the term of this patent is extended or adjusted under 35 U.S.C. 154(b) by 580 days.

(21) Appl. No.: 16/474,257

(22) PCT Filed: Jan. 15, 2018

(86) PCT No.: PCT/EP2018/050819
§ 371 (c)(1),
(2) Date: Jun. 27, 2019

(87) PCT Pub. No.: WO2018/130678
PCT Pub. Date: Jul. 19, 2018

(65) Prior Publication Data
US 2020/0127809 A1     Apr. 23, 2020

Related U.S. Application Data

(60) Provisional application No. 62/445,947, filed on Jan. 13, 2017.

(51) Int. Cl.
*H04L 9/00*       (2022.01)
*G16H 30/20*    (2018.01)
(Continued)

(52) U.S. Cl.
CPC .............. *H04L 9/001* (2013.01); *G01R 33/54* (2013.01); *G16H 30/20* (2018.01); *H04L 1/0061* (2013.01);
(Continued)

(58) Field of Classification Search
CPC ......... H04L 9/001; H04L 1/0061; H04L 9/14; H04L 9/304; H04L 27/001; H04L 27/36;
(Continued)

(56) References Cited

U.S. PATENT DOCUMENTS 6,356,780 B1   3/2002   Licato et al.
8,019,118 B2*   9/2011   Sternberg ............... G06V 20/40
                                                              382/100
(Continued)

FOREIGN PATENT DOCUMENTS

CN         103916234 A     7/2014
WO     WO-2018130678 A1 *   7/2018       ............. H04L 9/304

OTHER PUBLICATIONS

International Search Report From PCT/EP2018/050819 dated Apr. 19, 2018.
(Continued)

*Primary Examiner* — Hosuk Song

(57) ABSTRACT

A method for communicating magnetic resonance imaging (MRI) information wirelessly includes detecting an MRI system emission sequence, and identifying at least one parameter of the sequence. The at least one parameter identified is cross-correlated. A first initial condition for a first chaotic coded sequence and a second initial condition for a second chaotic coded sequence are determined based on the at least one parameter. The method further includes obtaining, from a modulation symbol mapped to MRI information generated at a local coil responsive to the sequence, a real component of the symbol and an imaginary compo-
(Continued)

nent of the symbol. The real component of the symbol is encrypted based on the first initial condition, and the imaginary component of the symbol is encrypted based on the second initial condition. The encrypted real component and imaginary component of the symbol are wirelessly transmitted.

20 Claims, 8 Drawing Sheets

(51) Int. Cl.
  *H04L 27/00* (2006.01)
  *H04L 27/36* (2006.01)
  *G01R 33/54* (2006.01)
  *H04L 1/00* (2006.01)
  *H04L 9/14* (2006.01)
  *H04L 9/30* (2006.01)
  *H04L 67/12* (2022.01)
  *H04W 12/041* (2021.01)
  *H04W 12/0431* (2021.01)

(52) U.S. Cl.
  CPC ........... *H04L 9/14* (2013.01); *H04L 9/304* (2013.01); *H04L 27/001* (2013.01); *H04L 27/36* (2013.01); *H04L 67/12* (2013.01); *H04W 12/041* (2021.01); *H04W 12/0431* (2021.01)

(58) Field of Classification Search
  CPC ..... H04L 67/12; G16H 30/20; H04W 12/041; H04W 12/0431; G01R 33/54; G06F 21/72
  See application file for complete search history.

(56) References Cited

U.S. PATENT DOCUMENTS

| | | | |
|---|---|---|---|
| 8,435,167 B2* | 5/2013 | Oohashi | A61M 21/02 600/27 |
| 8,542,716 B2 | 9/2013 | Chester et al. | |
| 9,471,748 B2* | 10/2016 | Liu | A61M 5/007 |
| 9,554,738 B1* | 1/2017 | Gulati | A61B 5/0075 |
| 10,489,118 B2* | 11/2019 | Dale | G06F 7/58 |
| 2009/0189988 A1 | 7/2009 | Jia et al. | |

OTHER PUBLICATIONS

Minh-Chinh Truong et al "On the Implementation of Chaotic Compressed Sensing for MRI" 2016 International Conference on Advanced Technologies for Communications IEEE Oct. 12, 2016, p. 103-107.

Wei Zhang, Chongfu Zhang, Wei Jin, Chen Chen, Ning Jiang and Kun Qiu, "Chaos Coding Based QAM IQ-Encryption for Improved Security in OFDM-PON", vol. 26, No. 19, IEEE Photonics Technology Letters, Oct. 2014, pp. 1964-1967.

G. Heidari-Bateni et al "Chaotic sequences for spread spectrum: an alternative to PN-sequences", IEEE ICSTWC, 2, pp. 74-80, Jan. 2013.

S. Fong-In et al., A Header Encryption of Ultrasound Image using Absolute-Value Chaotic Map; The 2014 Biomedical Engineering International Conference , Nov. 26-28, 2014.

Meghdad Ashtiyani et al., "Chaos-Based Medical Image Encryption Using Symmetric Cryptography" 2008 3rd International Conference on Information and Communication Technologies: From Theory to Applications; Apr. 7-11, 2008.

Hassan Noura et al., "Design of a Fast and Robust Chaos-Based CryptoSystem for image encryption" IEEE—IET Electronic Library (IEL) Conference Proceedings Jun. 10-12m, 2010.

Gayatri M. Vengurlekar et al., Encryption of Patient's Details Using Chaos Encryption; International Journal of Computer Informatics and Technological Engineering, vol. 2 Jun. 2015.

* cited by examiner

CHAOS CODING BASED COMMUNICATIONS FOR MRI COILS

CROSS REFERENCE TO RELATED APPLICATIONS

This application is a U.S. national phase application of International Application No. PCT/EP2018/050819 filed on Jan. 15, 2018, which claims the benefit of U.S. Provisional Application Ser. No. 62/445,947 filed on Jan. 13, 2017 and is incorporated herein by reference.

BACKGROUND

Magnetic resonance imaging (MRI) systems use local radio frequency coils placed on or around a subject (patient) to receive signals of the subject and transmit data of the received signals to the MRI system for processing and analyzing. The local radio frequency coils may transmit the data via, for example, a coaxial cable or fiber optics.

If the magnetic resonance imaging systems and local radio frequency coils are to be modified to communicate via wireless transmissions, the wireless transmissions need to be both reliable and secure, and should not result in unnecessary processing delays. For example, undetectable errors in data resulting from wireless transmissions might affect a diagnosis or treatment for a subject being imaged by a magnetic resonance imaging system. Additionally, security of data should not be unnecessarily compromised simply due to the use of wireless transmissions. Moreover, a link delay between local radio frequency coils (or Mobile Stations (MSTs)) and the magnetic resonance imaging systems (or Base Stations (BSTs)) should be kept as small as possible, even if this imposes a significant constraint on the amount of signal processing the transmission-reception (Tx-Rx) path can tolerate.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
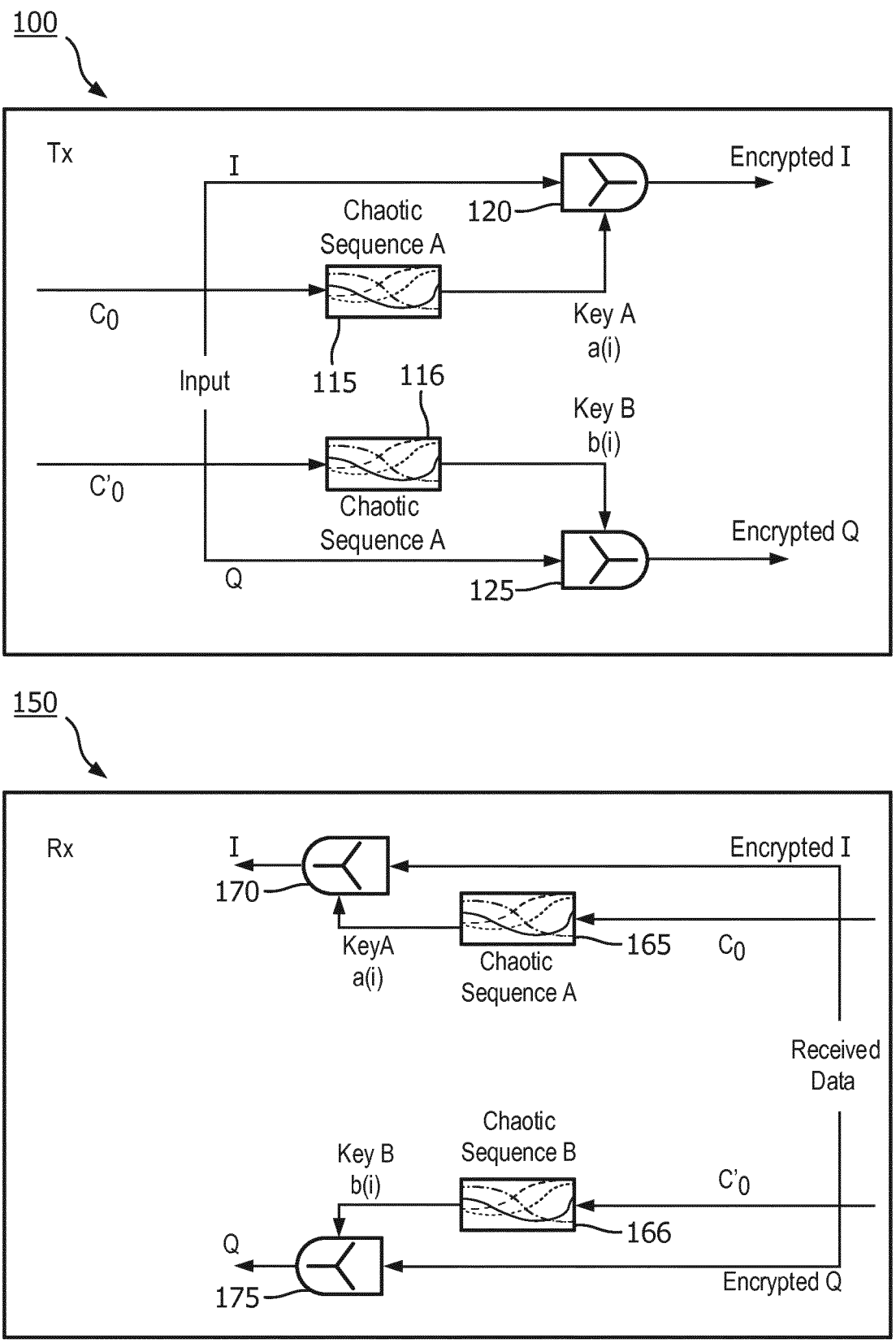
FIG. 1 is a view of an encryption/decryption system for chaos coding based communications for MRI coils in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, chaos coding based communications for MRI coils includes a variety of combined features to ensure accuracy and safety for wireless communications, while still providing a fast processing capability. Broadly speaking, chaos coding is used herein by setting initial conditions which are mapped via chaos/chaotic maps to generate/output encryption keys. The initial conditions are based on operational parameters from an MRI system, so that the encryption keys will vary for each different operation of the MRI system. Thus, the setting the initial conditions and the actual encrypting may be considered separate processes as described herein.

Chaos coding employs the branch of mathematics known as chaos theory. Chaos theory involves the behavior of dynamical systems that are extremely sensitive to initial conditions. That is, in dynamical systems, small differences in initial conditions are correlated with widely divergent outcomes, even though the future behavior (outcomes) are determined entirely by the initial conditions. The mapping involved in chaos coding is the process by which an initial condition is input to a model of a dynamical system (a "chaotic map") to produce an outcome. This mapping may also be known as logistic mapping. As described herein, the output of the model (chaotic map) is a different encryption key for each different initial condition input to the model.

The encryption keys output from a chaotic map can be used in encrypting wireless communications including, for example, modulation symbols such as quadrature amplitude modulation (QAM) signals. In QAM communications, a carrier signal is modified in accordance with symbols representing digital data being transmitted. QAM signals are thus embodied by the symbols, which in turn are representative of the underlying digital data. Real I and imaginary Q components of QAM signals are obtained by a form of mapping different than that described above for chaos coding. That is, the real I and imaginary Q components of QAM signals are obtained in a process known as constellation mapping. Therefore, according to the present disclosure, chaotic mapping can be used to obtain encryption keys based on initial conditions, and constellation mapping can be used to obtain the real I and imaginary Q components of QAM signals which can then be encrypted using the encryption keys. To be clear, QAM is just an example of the forms of modulation that can be used in accordance with the teachings herein.

FIG. 1 is a view of an encryption/decryption system for chaos coding based communications for MRI coils in accordance with a representative embodiment. In FIG. 1, encryption is performed by an encryption system 100, and decryption is performed by a decryption system 150. For the encryption system 100, a first initial condition $C_0$ is input to a chaotic sequence A map 115. A second initial condition $C'_0$ is input to a chaotic sequence B map 116. The chaotic sequence A map 115 and chaotic sequence B map 116 are each used to generate encryption keys as outputs. The output of chaotic sequence A map 115 is shown as Key A, and the output of chaotic sequence B map 116 is shown as Key B. In other words, encryption sequence keys (Key A and Key B) are composed by chaotic coded sequences. In FIG. 1, the first initial condition $C_0$ and second initial condition $C'_0$ are assumed as inputs to the encryption system 100 and decryption system 150. The process of setting the first initial condition $C_0$ and second initial condition $C'_0$ is described beginning for FIG. 2. However, for the purposes of describing the encryption in FIG. 1, the first initial condition $C_0$ and second initial condition $C'_0$ can vary for each operation of an MRI system so that the encryption method varies for each transmission such that the MRI sequences are not fixed whereas the chaotic sequences keep their nature.

Additionally, the chaotic sequence A map 115 and chaotic sequence B map 116 may be implemented using a software program stored in a memory and executed by a processor. That is, the process for applying the chaotic sequence A map 115 and chaotic sequence B map 116 to initial conditions $C_0$ and $C'_0$ may be performed by executing software instructions using a processor to generate the resultant encryption sequence keys (Key A and Key B).

In FIG. 1, the label "I" designates the real component of a modulation symbols (e.g., a QAM symbol) used to carry magnetic resonance imaging information. The label "Q" designates the imaginary component of the modulation symbols (e.g., the QAM symbol) used to carry magnetic resonance imaging information. The magnetic resonance imaging information from which I and Q are derived is labeled as Input in FIG. 1. The encryption mechanism starts with the constellation mapping that produces the I and Q values. The inputs I and Q can be derived from a modulator (e.g., a QAM modulator) as shown later for FIG. 2, but such constellation mapping can be extended to any I and/or Q mapping encoding. The separated real I and imaginary Q are encrypted with Key A and Key B (a(i) and b(i)) respectively. The real component I is encrypted by encryption engine 120 using Key A. The imaginary component Q is encrypted by encryption engine 125 using key B. The output of encryption engine 120 is labeled "Encrypted I", and the output of encryption engine 125 is labeled "Encrypted Q".

The encryption process described herein can be performed by multiplying I and Q parts of a symbol by the pair of encryption keys Key A and Key B (sequences a(i), b(i)) separately. This can be represented as:

$$x = \text{Re}\{w\}*a(i) + j\,\text{Im}\{w\}b(i) \qquad (1)$$

where $\text{Re}\{\cdot\}$ and $\text{Im}\{\cdot\}$ indicate the real and imaginary values respectively, w represents the current symbol being transmitted and $a(i), b(i) \in \{1, -1\}$ are the elements of two different sequences. That is, a(i) and b(i) are generated by applying initial conditions to a chaotic map or chaotic maps. As an example, the modified chaotic mapping [2] below shows the chaos model defined by the following iterative formula:

$$c_{n+1} = f(c_n) = 1 - \mu c_n^2, \mu \in \{1.40015, 2\}, c^n \in (-1, 1) \qquad (2)$$

$$s_n = \text{sgn}(c_n) \qquad (3)$$

where $\text{sgn}(\cdot)$ denotes the sign function and sn is the n-th element of the generated chaotic sequence. $c_n$ is the n-th state value of equation (2), and c0 is an arbitrary value between −1 and 1, provided by the MRI system/sequence, and μ is the bifurcation parameter. As in [1], this scheme takes the initial value $c_0$, the bifurcation parameter μ, and the iteration step N as the security keys. After iteration with step N, the formula falls into the fully chaotic domain and the sequence can be obtained by (3).

For the decryption system 150, the encrypted I output by encryption engine 120 is input to decryption engine 170. The encrypted Q output by encryption engine 125 is input to decryption engine 175. The first initial condition $C_0$ is input to the chaotic sequence A map 165 which corresponds to chaotic sequence A map 115 in the encryption system 100. The second initial condition $C'_0$ is input to the chaotic sequence B map 166 which corresponds to chaotic sequence B map 116 in the encryption system 100. The chaotic sequence A map 165 and chaotic sequence B map 166 are each used to generate decryption keys as outputs. The output of chaotic sequence A map 165 is shown as Key A (a(i)), and the output of chaotic sequence B map 166 is shown as Key B (b(i)).

In FIG. 1, the real component I of the original symbol is derived from the decryption engine 170 when Key a(i) is input to decrypt encrypted I. The imaginary component Q of the original symbol is derived from the decryption engine 175 when Key b(i) is input to decrypt encrypted Q.

At the receiver side (Rx) shown in FIG. 1, the decryption process takes place similar to the encryption process. A formula that describes the decryption process can be explained as $$w' = \mathrm{Re}\{x'\} * a(i) + j\,\mathrm{Im}\{x'\} b(i) \qquad (4)$$

where x' is the received symbol.

In FIG. 1, the encryption system 100 can be provided at the PHY level of a communications link attached to, incorporated in, or otherwise integrated with a radio frequency coil. The link delay between such a radio frequency coil (or Mobile Station (MST)) and the overall MRI system (or Base Station (BST)) should be kept as small as possible for a variety of reasons. Providing the encryption system 100 at the PHY level provides for a lower level of signal processing insofar as error detection and correction can also be provided at the PHY level.

In terms of error detection and correction at the PHY level, forward error correction (FEC) codes can be used together with a cycle redundancy code (CRC). Since forward error correction codes and cycle redundancy codes can already be implemented at the PHY layer, implementing the encryption system 100 also at the PHY layer can lead to efficiency and processing gains. The arrangement described herein using the PHY layer also allows an MRI communications system to meet latency requirements. Secure transfers in the PHY layer also reduce the signal processing power required for the processing described herein.

The encrypting described above is based on chaotic sequences, by which transmitted modulation symbol (e.g., QAM symbol) real (I) and complex (Q) portions are encrypted separately. Chaotic sequences can be detected by authorized receivers under noisy environments, so security is increased and not compromised. The encryption and decryption key sequences for encryption and decryption are generated using chaotic mapping, and chaotic maps have properties (e.g., ergodicity) that allow for high sensitivity to initial conditions and control parameters that make the implementation complexity low. Additionally, in the systems and methods described herein, complete wireless MRI data transmissions (i.e., data, data headers and control signals) can be encrypted, providing a high level of security.

Figure 2:
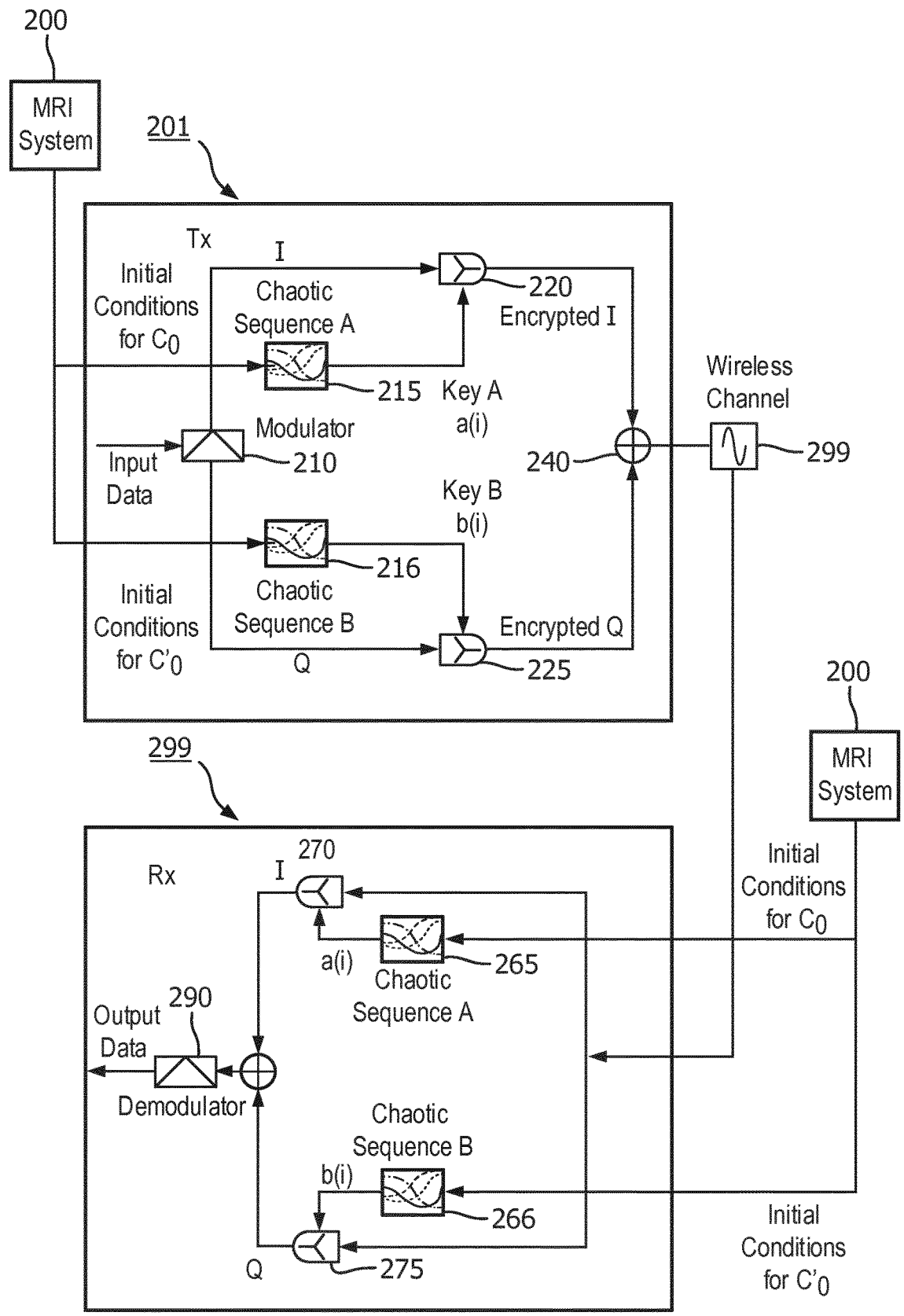
FIG. 2 is a view of a communications system that includes both transmission and reception sections for chaos coding based communications for MRI coils in accordance with a representative embodiment.

FIG. 2 is a view of a communications system that includes both transmission and reception sections for chaos coding based communications for MRI coils in accordance with a representative embodiment. In FIG. 2, an MRI system 200 is shown as the source for inputs to communications links 201 and 299, though the MRI system 200 here should be considered to also include local coils. The communications link 201 includes an encryption subsystem such as the encryption system 100 shown in FIG. 1. The communications link 299 includes a decryption subsystem such as the decryption system 150 shown in FIG. 1.

In FIG. 2, the MRI system 200 along with local coils are the source of magnetic resonance imaging information. Overall operation of an MRI system 200 is explained in more detail later with respect to FIGS. 6 and 7, as for now a brief description should suffice. An MRI system 200 uses a variable sequence in a transmit stage to selectively deliver a B1 field to a subject via radio frequency (RF) coils. In a receive stage, the hydrogen atoms that are stimulated by the B1 field return to an original position (i.e., the position before the selective delivery of the B1 field) and emanate a weak radio frequency signal which can be picked up by the local coils (local radio frequency coils on or near the body of the subject) and used to produce images. The magnetic resonance imaging information includes the information from the weak radio frequency signals that are detected by the local coils placed specifically to pick up the weak radio frequency signals from the hydrogen atoms of the human body. The magnetic resonance imaging information received, generated, identified etc. by the local coils is also at least part of the information communicated wirelessly as described herein.

The chaotic coded sequences described with respect to FIGS. 1 and 2 can be generated using, or determined by, unique MRI parameters. The unique MRI parameters may be a variety of parameters of an MRI transmission (TX) sequence, including the sequence itself, and/or a variety of parameters of a subject (patient) reception (RX) signal. As a result, the encryption method can vary for each transmission. In addition to the MRI sequence parameters, initial conditions can also vary based on e.g., environment or subject (patient) information so that, every data transmission has a different and unique encryption key. The encryption described herein has very low probability of being compromised since the initial conditions are only known a priori to the system, and unique keys are not transmitted over the air since they are known and generated or determined by parameters of the MRI system 200.

In FIG. 2, the communications link 201 receives the initial conditions $C_0$ and $C'_0$ as well as the input data of the magnetic resonance imaging information. A modulator (e.g., QAM modulator) 210 (mapper) maps the input magnetic resonance imaging information to a modulation symbol (e.g., a QAM symbol). The modulation symbol is then divided into a real component I and an imaginary component Q, which are subsequently separately subject to encryption by encryption engines 220 and 225 respectively.

The first initial condition $C_0$ is used by chaotic sequence A map 215 to generate encryption Key A. Encryption Key A in turn is used to encrypt the real component of the modulation symbol (e.g., QAM symbol) I. The second initial condition $C'_0$ is used by chaotic sequence B map 216 to generate encryption Key B. Encryption Key B in turn is used to encrypt the imaginary component of the modulation symbol (e.g., QAM symbol) Q. The encrypted I and encrypted Q are then combined, for example, via parallel to serial conversion, or via, for example, inverse fast fourier transform (IFFT) processing in transmitter 240 and put onto a communication line 299, which may be a wireless communications system comprising one or more wireless channels. Of course, any linear operation including linear transformations such as IFFT can be used to combine encrypted I and encrypted Q.

The communications link 299 performs a process that is essentially the opposite of the processing by the communications link 201. The communications link 299 receives the initial conditions $C_0$ and $C'_0$ from the MRI system 200, and receives the combined encrypted I and encrypted Q from the communication link 299. The initial conditions $C_0$ and $C'_0$ are put through chaotic sequence A map 265 and chaotic sequence B map 266 respectively to obtain decryption keys a(i) and b(i). Decryption engines 270 and 275 use the decryption keys a(i) and b(i) to obtain the real component I and imaginary component Q of the original modulation symbol that carries the original magnetic resonance imaging information. Demodulator 290 (e.g., QAM demodulator) demodulates the real component I and imaginary component Q to output the same magnetic resonance imaging information that was previously input to the communications link 201.

As explanation of the context of communications links 201 and 299 in FIG. 2, these communications links 201, 299 may be in the same room or in the same building. For example, communications link 201 may be attached to, or even built into, one of the local coils that receives the weak radio frequency signals from the body of the subject. Communications link 299 may be attached to a wall of a room that includes the MRI system 200, and then feeds the magnetic resonance imaging information to a computer for processing. Thus, the communications links 201, 299 may avoid any need for cabling between the local coil and the MRI system 200, such that the local coils can be made portable, exchangeable, interchangeable etc.

Figure 3:
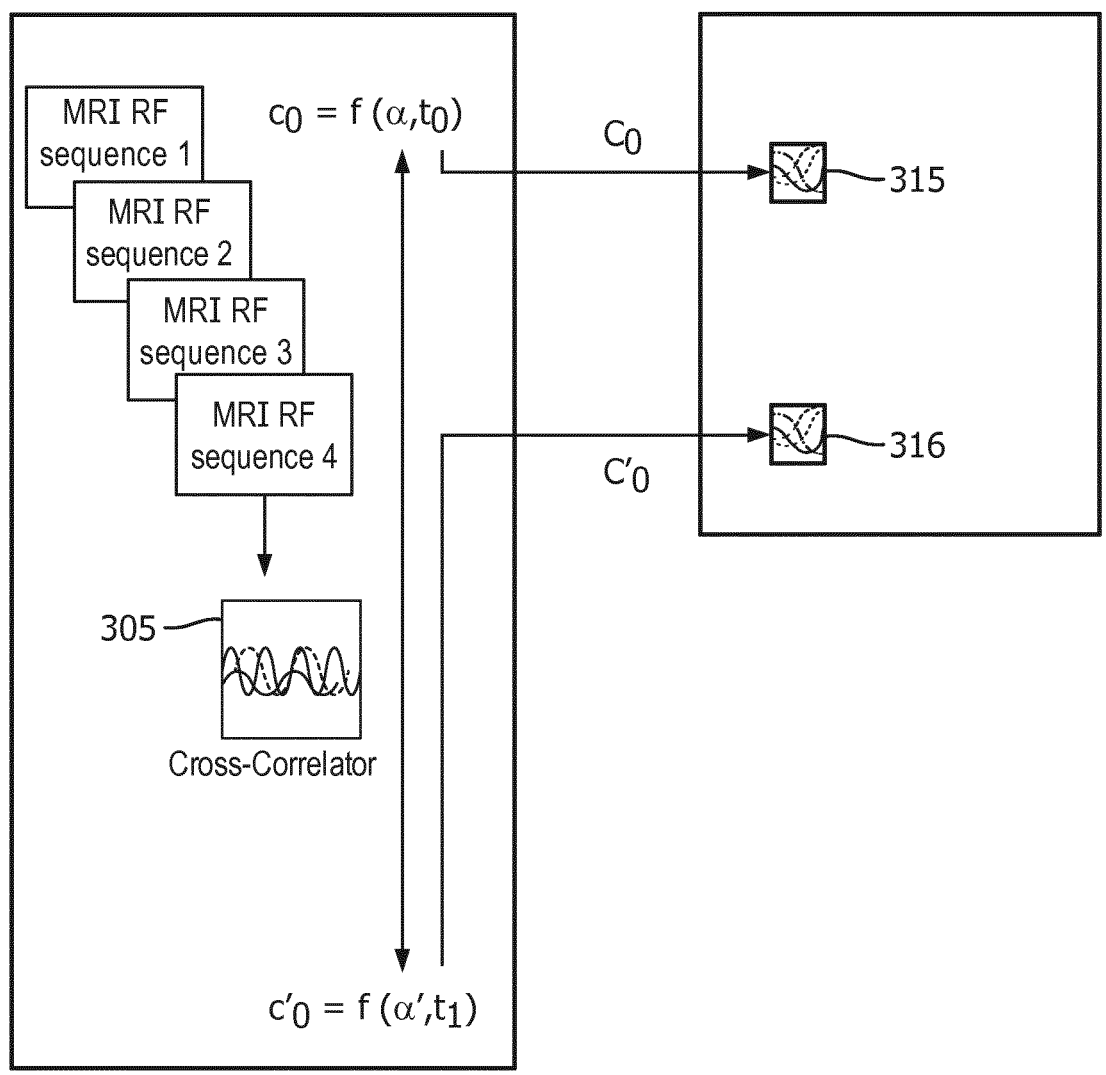
FIG. 3 is another view of a communications system for chaos coding based communications for MRI coils in accordance with a representative embodiment.

FIG. 3 is another view of a communications system for chaos coding based communications for MRI coils in accordance with a representative embodiment. FIG. 3 illustrates the process of obtaining and conveying initial conditions $C_0$ and $C'_0$. As explained with respect to FIGS. 1 and 2, the initial conditions $C_0$ and $C'_0$ are processed through chaotic sequence A maps 115/215 and chaotic sequence B maps 116/216 to generate Key A and Key B respectively. In FIG. 3, information from an MRI radio frequency sequence is input to a cross-correlator 305 to produce the initial conditions $C_0$ and $C'_0$. The MRI radio frequency information may be the pattern of the sequence (similar to a morse code pattern), starting and ending time of the sequence, duration of the sequence, signal characteristics of the sequence, and so on. Each different MRI radio frequency sequence will result in a different set of initial conditions $C_0$ and $C'_0$ being output from the cross correlator 305. The initial conditions are entered into chaotic sequence A map 315 and chaotic sequence B map 316 respectively, to generate encryption Key A and encryption Key B respectively as output. Incidentally, cross-correlation is a known measure of determining similarity of two series as a function of the difference between the two. According to the present disclosure, cross-correlation can be applied to multiple different series of different parameters to identify the best correlation(s). As should be clear, cross-correlation can be performed using software instructions stored in a memory and executed by a processor.

As described above, the initial condition values $c_0$ and $c'_0$ are generated via the cross-correlation function of the MRI sequences used to perform the MRI scan for a specific subject as shown in FIG. 3. The $c_0$ and $c'_0$ values are functions of the correlation factors α and α' and a time stamp t0 and t1 respectively.

As mentioned previously, the process of generating initial conditions $c_0$ and $c'_0$ may be considered a separate process from the actual encryption process. Whereas the encryption process described herein is typically performed by a communications link integrated with a local coil, the generation of initial conditions may be performed fully, partly or not at all at the communications link. That is, the initial conditions $c_0$ and $c'_0$ may be provided directly from the MRI system 200 (in FIG. 2), e.g., at the time the MRI sequence is confirmed before emission. The initial conditions $c_0$ and $c'_0$ may also be generated at the communications link that includes the encryption system 100, or in part at the MRI system 200 and in part at the communications link that includes the encryption system 100. Insofar as encryption keys Key A and Key B are generated before emissions from the MRI system 200, these Keys A and B are uncorrelated to the channel conditions. As a result, statistical properties are not exposed once the MRI sequences are emitted. In sum, the initial conditions will be built based on the MRI sequences at a specific time stamp such that the normalized correlation factors provide the initial condition values c0 and c'0 as indicated in equation (2) above. The cross-correlator 305 in FIG. 3 may therefore be provided at either the communications links, or at the MRI system 200 (in FIG. 2).

Figure 4:
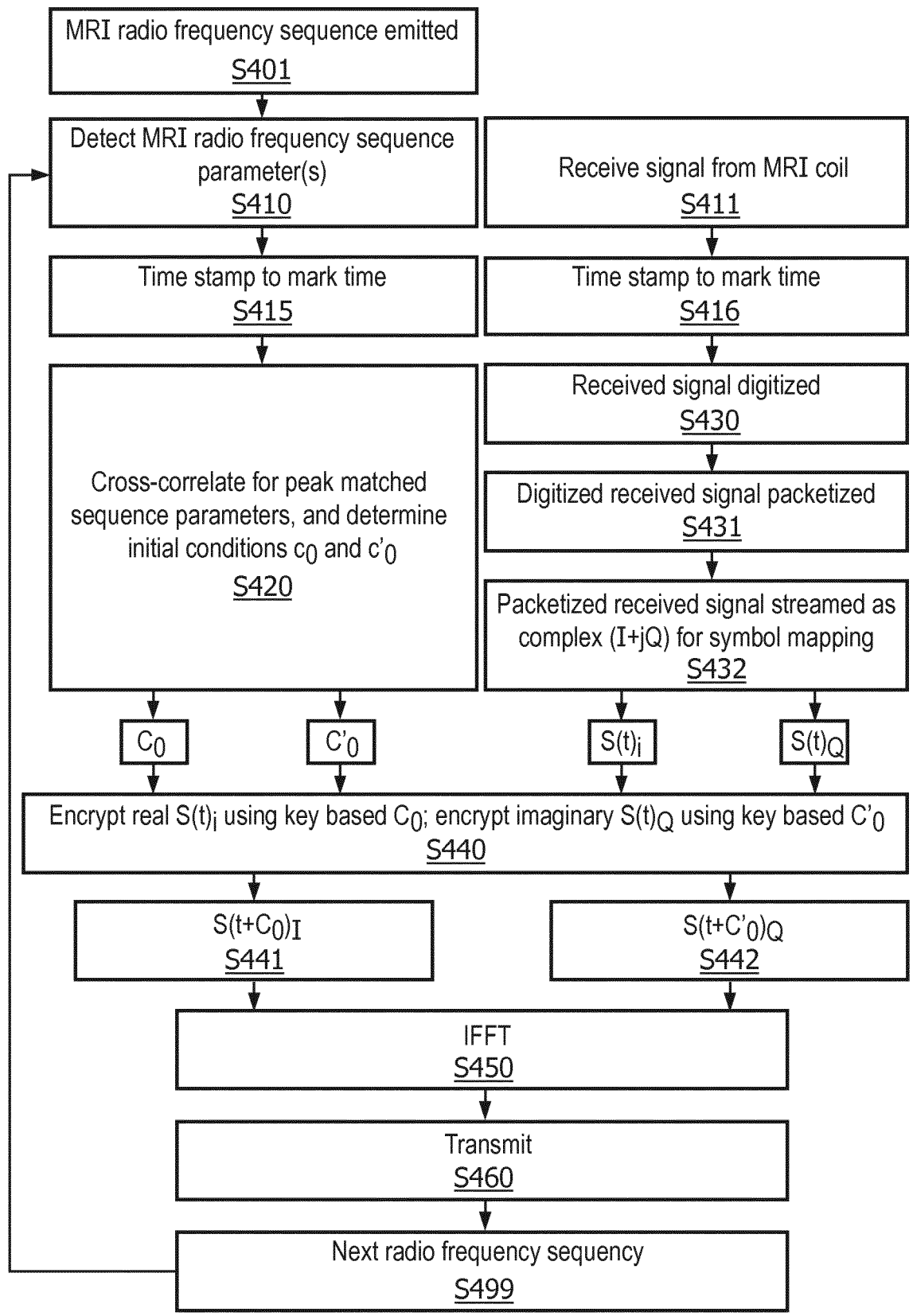
FIG. 4 is a view of a transmission process for chaos coding based communications for MRI coils in accordance with a representative embodiment.

FIG. 4 is a view of a transmission process for chaos coding based communications for MRI coils in accordance with a representative embodiment. In FIG. 4, the process shown is partially parallel, as one or more features are not necessarily performed by communications units such as communications link 201. At S401, an MRI radio frequency sequence is emitted by a system such as MRI system 200. At S410, the MRI radio frequency sequence parameter(s) are detected by, for example, a communications link 201. At S415, a time stamp is applied to mark the time at which the MRI radio frequency sequence parameter(s) are detected.

At S411, a signal from the MRI local coil is received. The signal from the MRI local coil is the information from the subject of the MRI session. At S416, a time stamp is applied to mark the time at which the signal is received from the MRI local coil. The time stamps at S415 and S416 may be correlated to each other, such as to identify any offset.

At S420, the MRI radio frequency sequence parameters are cross-correlated to identify a peak (i.e., best) match among multiple parameters. The peak match among the cross-correlated MRI radio frequency sequence parameters is used to determine the initial conditions $C_0$ and $C'_0$. The output of S420 is the initial conditions $C_0$ and $C'_0$.

At S430, the signal received form the MRI local coil is digitized, and at S431 the digitized received signal is packetized. At S432, the packetized received signal is subject to mapping (e.g., QAM mapping), and separated and streamed as a complex (I+jQ) set of information for encryption. The output of S432 is the stream of separated real (I) and imaginary (Q) signals $S(t)_I$ and $S(t)_Q$.

At S440, the streams of real signals $S(t)_I$ and $S(t)_Q$ are separately encrypted using the Keys derived from the Chaotic Sequence A map and Chaotic Sequence B map respectively. The separate encrypted stream $S(t+C_0)_I$ is sent at S441, and the separate encrypted stream $S(t+C'_0)_Q$ is sent at S442. At S450, the two separate encrypted streams $S(t+C_0)_I$ and $S(t+C'_0)_Q$ are subject to inverse fast fourier transformation, and the resultant stream is wirelessly transmitted at S460. As noted previously, any linear operation including linear transformations can be used to combine the encrypted streams $S(t+C_0)_I$ and $S(t+C'_0)_Q$. At S499, the process moves to the next radio frequency sequence and repeated beginning at S410 and S411.

Of course, when an unauthorized local coil is used in a system that communicates using the chaos coding based communications for MRI coils described herein, the method of FIG. 4 will provide security that prevents such use. That is, an MRI system that communicates wirelessly with the expectation that a specific encryption system will be followed will not allow such communications with local coils that are not equipped to implement the encryption. Additionally, the methods of FIG. 4 can also be used to block hackers, improve jamming performance for wireless coils, and so on.

Figure 5:
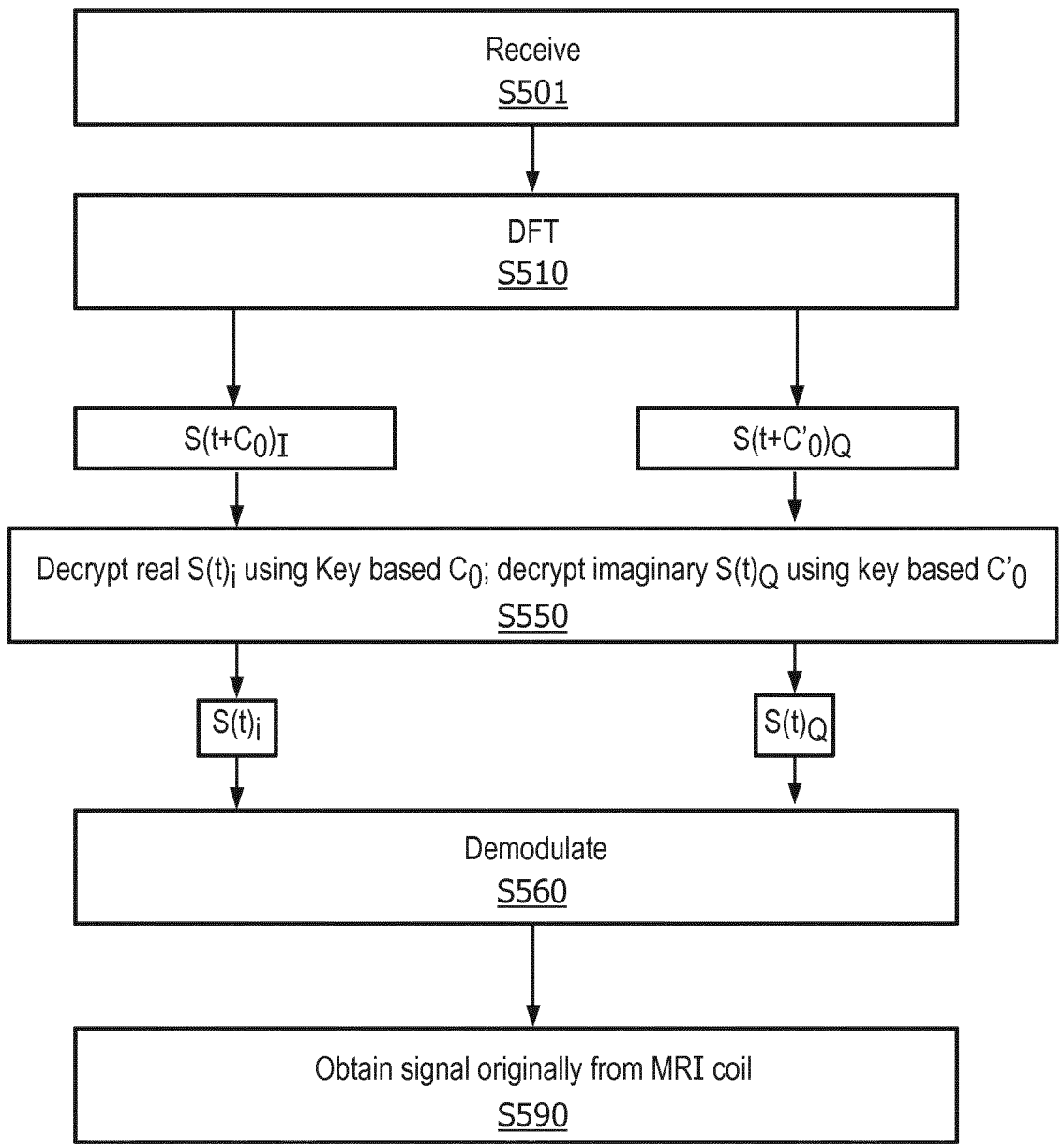
FIG. 5 is a view of a reception process for chaos coding based communications for MRI coils in accordance with a representative embodiment.

FIG. 5 is a view of a reception process for chaos coding based communications for MRI coils in accordance with a representative embodiment. In FIG. 5, the encrypted stream transmitted wirelessly at S460 is received, such as by a communications link 299 at S501. At S510 a discrete fourier transformation (DFT) is performed. The DFT in FIG. 5 is exemplary, as the actual process at S510 is the inverse of the linear process performed at S450, and the linear process performed at S450 does not have to be a transformation let alone an IFFT. At S550, the streams are decrypted after being separated, such as by demultiplexing. The result of the decryption is the stream of separated real (I) and imaginary (Q) signals $S(t)i$ and $S(t)_Q$. The signals $S(t)i$ and $S(t)_Q$ are then demodulated at S560. The original signal with the magnetic resonance imaging information from the MRI local coil is obtained at S590. Thus, the magnetic resonance imaging information from the MRI local coil can be securely transmitted in a local environment and used by a computer for processing.

Figure 6:
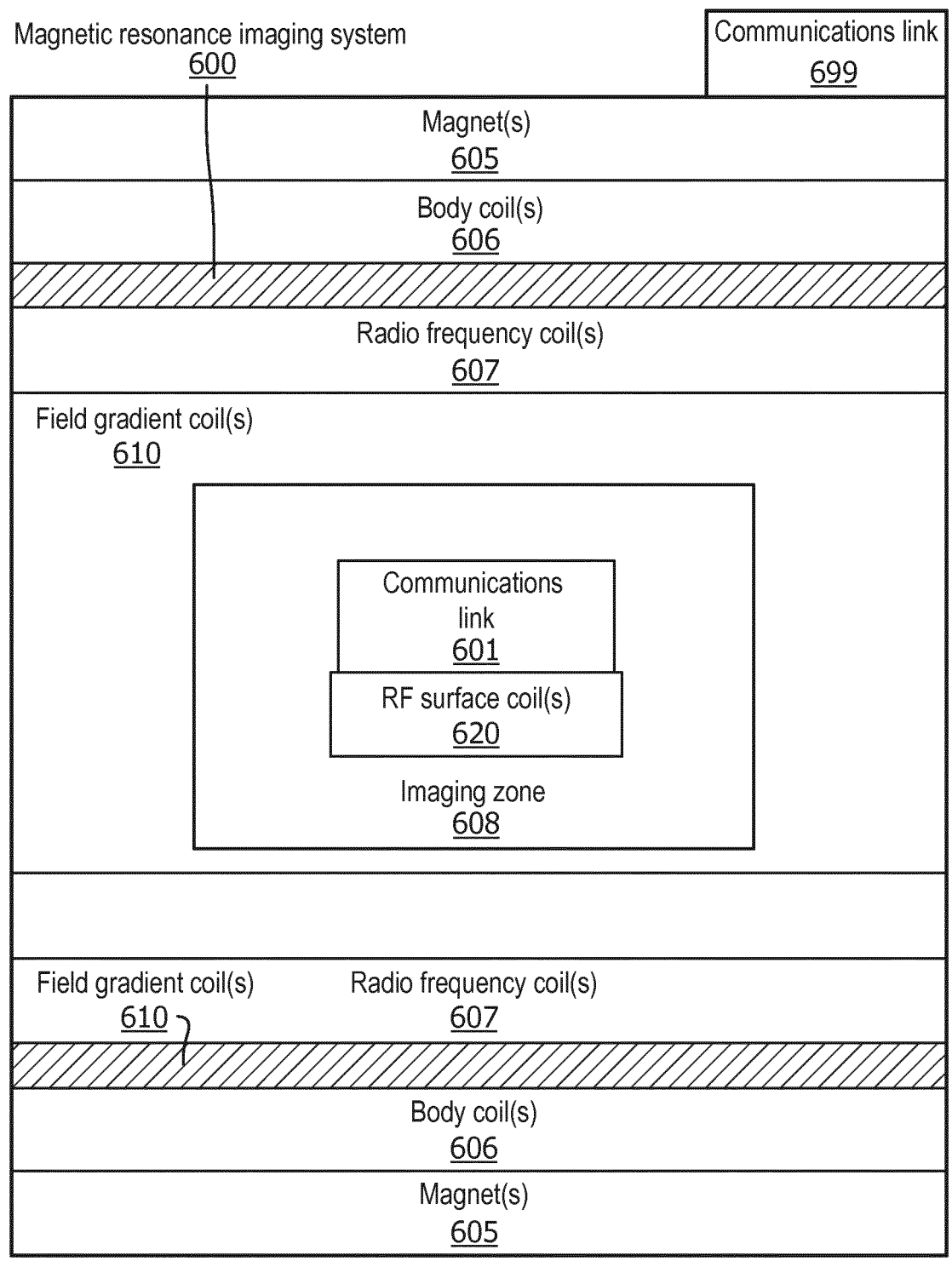
FIG. 6 is a view of an MRI system for chaos coding based communications for MRI coils in accordance with a representative embodiment.

FIG. 6 is a view of an MRI system for chaos coding based communications for MRI coils in accordance with a representative embodiment. In FIG. 6, a magnetic resonance imaging system 600 includes outer magnet(s) 605, body coil(s) 606, field gradient coil(s) 610, and radio frequency coil(s) 607. RF surface coil(s) 620 are provided in the imaging zone 608, i.e., on or about the body of the subject. The RF surface coils 620 are local coils to which communications units such as communications links 201 are attached, embedded, integrated etc. Communications units The radio frequency surface coil(s) 620 are provided to pick up the radio frequency signals emanating from the hydrogen atoms in the subject being imaged. For this reason, the radio frequency surface coil 620 is shown low in the imaging zone 608, with the understanding that the radio frequency surface coil(s) 620 will be placed on or near the subject being imaged.

Figure 7:
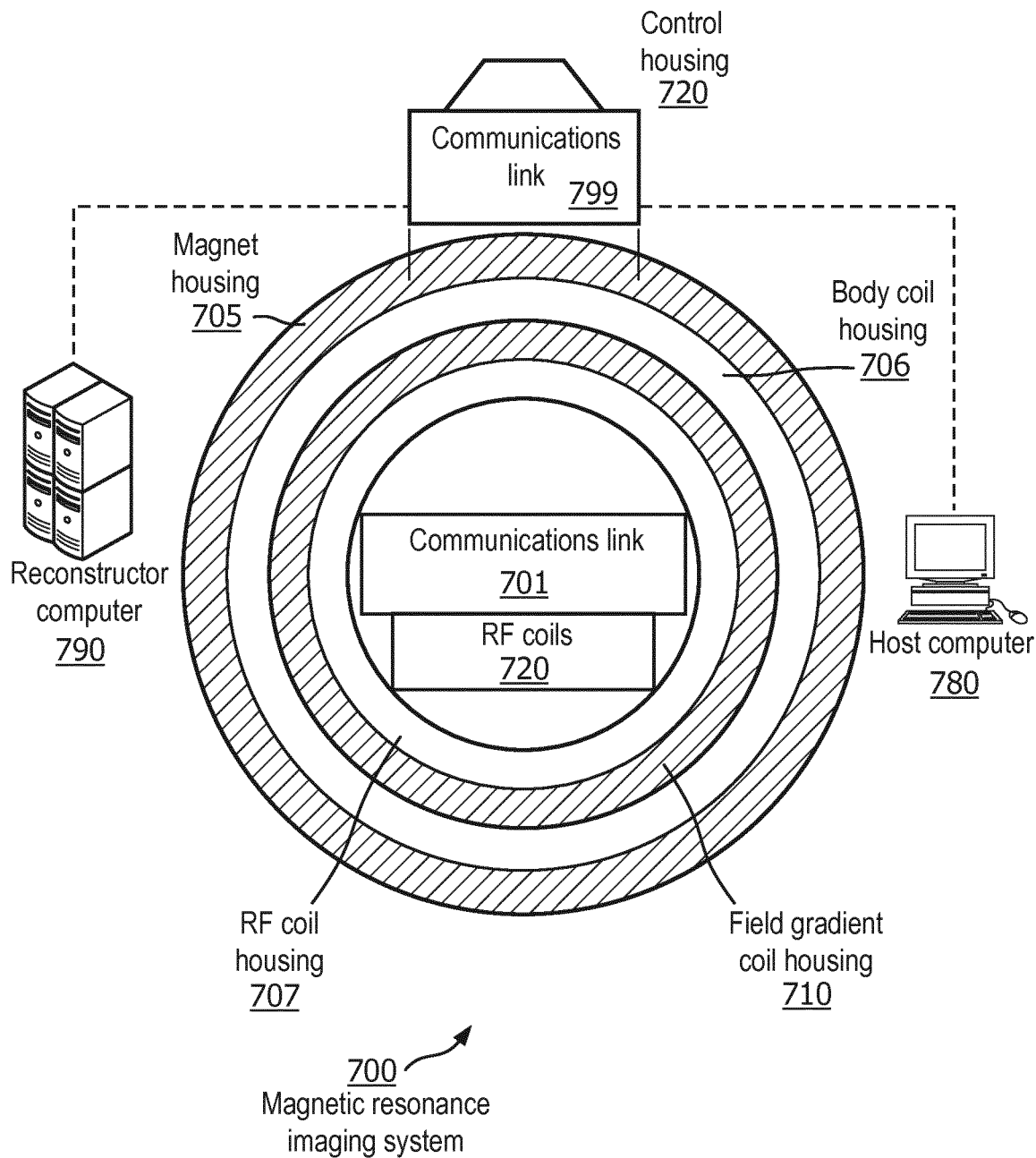
FIG. 7 is another view of an MRI system for chaos coding based communications for MRI coils in accordance with a representative embodiment.

FIG. 7 is another view of an MRI system for chaos coding based communications for MRI coils in accordance with a representative embodiment. In FIG. 7, a magnet housing 705 is designated with a hatch pattern as an outer structure of a magnetic resonance imaging system 700. A body coil housing 706 is immediately interior to the magnet housing 705. A field gradient coil housing 710 is immediately interior to the body coil housing 706. A radio frequency (RF) coil housing 707 is immediately interior to the field gradient coil housing 710. A control housing 720 is provided on the magnet housing 705 to house, e.g., external circuitry such as a transceiver. The control housing 720 may house, for example, a communications unit such as communications link 299.

In FIG. 7, radio frequency coils 720 are body coils placed on the body of the subject (patient) who is subjected to the magnetic resonance imaging scan. The radio frequency signals are emitted from the magnetic resonance imaging system 700 to excite the hydrogen atoms, and the hydrogen atoms emanate a weak radio frequency signal.

Figure 8:
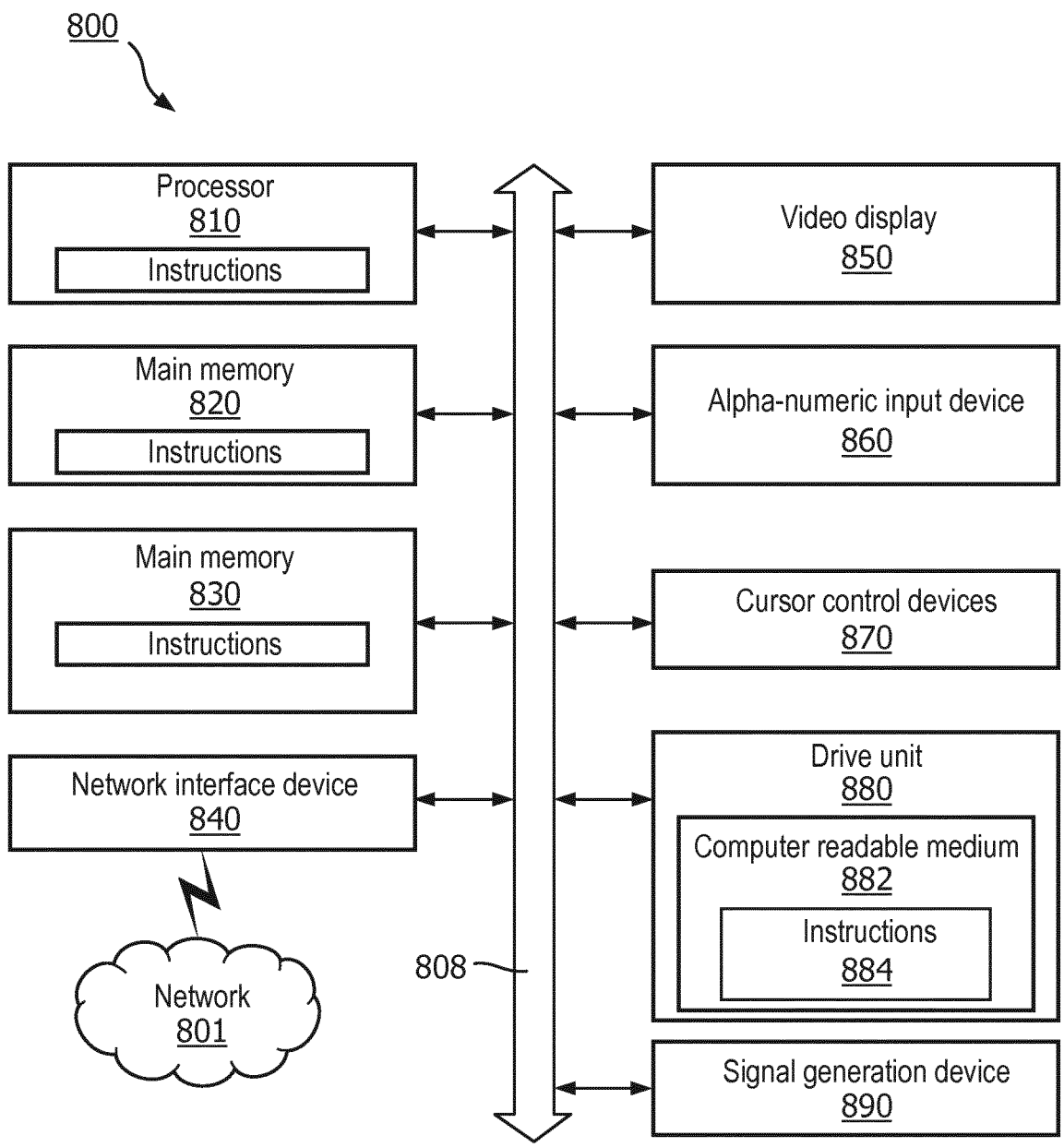
FIG. 8 is a view of an exemplary general computer system that includes a set of instructions for chaos coding based communications for MRI coils in accordance with a representative embodiment.

In FIG. 7, two computers included with the magnetic resonance imaging system 700 include the reconstructor computer 390 and the host computer 780. The host computer 780 interfaces with an operator of the magnetic resonance imaging system 700 to control the magnetic resonance imaging system 700 and to collect the images. The reconstructor computer 790 is a "background" computer that acts as a gatekeeper for data flow. The reconstructor computer 790 does not interact with the operator. Although not shown in FIG. 7, data may also be taken offline so that analysis may be performed on a, for example desktop, computer using software that may be proprietary to the manufacturer of the magnetic resonance imaging system 700. FIG. 8 shows a general computer system that may partially or fully be used to implement the reconstructor computer 790 and host computer 780, as well as any other computer or computing device that performs part or all of methods described herein.

FIG. 8 is a view of an exemplary general computer system that includes a set of instructions for chaos coding based communications for MRI coils in accordance with a representative embodiment of the present disclosure. FIG. 8 is an illustrative embodiment of a general computer system, on which a method of chaos coding based communications for MRI coils can be implemented, and which is shown and is designated 800. The computer system 800 can include a set of instructions that can be executed to cause the computer system 800 to perform any one or more of the methods or computer based functions disclosed herein. The computer system 800 may operate as a standalone device or may be connected, for example, using a network 801, to other computer systems or peripheral devices.

In a networked deployment, the computer system 800 may operate in the capacity of a server or as a client user computer in a server-client user network environment, or as a peer computer system in a peer-to-peer (or distributed) network environment. The computer system 800 can also be implemented as or incorporated into various devices, such as a stationary computer, a mobile computer, a communications link, a reconstructor computer, a host computer, or any other machine capable of executing a set of instructions (sequential or otherwise) that specify actions to be taken by that machine. The computer system 800 can be incorporated as or in a device that in turn is in an integrated system that includes additional devices. Further, while a single computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 includes a processor 810. A processor for a computer system 800 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 800 is configured to execute software instructions to perform functions as described in the various embodiments herein. A processor for a computer system 800 may be a general-purpose processor or may be part of an application specific integrated circuit (ASIC). A processor for a computer system 800 may also be a microprocessor, a microcomputer, a processor chip, a controller, a microcontroller, a digital signal processor (DSP), a state machine, or a programmable logic device. A processor for a computer system 800 may also be a logical circuit, including a programmable gate array (PGA) such as a field programmable gate array (FPGA), or another type of circuit that includes discrete gate and/or transistor logic. A processor for a computer system 800 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 800 includes a main memory 820 and a static memory 830 that can communicate with each other via a bus 808. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a particular carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 800 may further include a video display unit 850, such as a liquid crystal display (LCD), an organic light emitting diode (OLED), a flat panel display, a solid-state display, or a cathode ray tube (CRT). Additionally, the computer system 800 may include an input device 860, such as a keyboard/virtual keyboard or touch-sensitive input screen or speech input with speech recognition, and a cursor control device 870, such as a mouse or touch-sensitive input screen or pad. The computer system 800 can also include a disk drive unit 880, a signal generation device 890, such as a speaker or remote control, and a network interface device 840.

In an embodiment, as depicted in FIG. 8, the disk drive unit 880 may include a computer-readable medium 882 in which one or more sets of instructions 884, e.g. software, can be embedded. Sets of instructions 884 can be read from the computer-readable medium 882. Further, the instructions 884, when executed by a processor, can be used to perform one or more of the methods and processes as described herein. In an embodiment, the instructions 884 may reside completely, or at least partially, within the main memory 820, the static memory 830, and/or within the processor 810 during execution by the computer system 800.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 882 that includes instructions 884 or receives and executes instructions 884 responsive to a propagated signal; so that a device connected to a network 801 can communicate voice, video or data over the network 801. Further, the instructions 884 may be transmitted or received over the network 801 via the network interface device 840.

Notably, computers in or around the immediate vicinity of a magnetic resonance imaging system 200, may vary from typical computers to ensure they do not interfere with the operation of the magnetic resonance imaging system 200. For example, a computer system 800 may be modified to ensure that it emits no or negligible magnetic or radio frequency transmissions.

Accordingly, chaos coding based communications for MRI coils enables error correction and prevention, secure wireless communications, and appropriate processing for the secure wireless communications. The chaos coding based communications for MRI coils can be implemented at the PHY OSI layer, rather than at a higher level such as the Medium Access Control (MAC) layer, to secure transmissions against information thefts.

Because of implementing the chaos coding based IQ encryption at the PHY layer level, there is no need for encryption at a higher layer, i.e. MAC. This reduces the signal processing time overhead and simplifies the overall communications system architecture.

Also, as described above, chaos coding based communications for MRI coils provides security and reliability, and can use a combination of, for example, forward error correction (FEC) and encryption blocks that meet latency requirements too. Accordingly, chaos coding based communications for MRI coils provides a secure system that still meets (any) delay requirements. The security of encryption can be used for both detection and prevention of non-authorized coils, as well as protection of the transfer of MRI data from hackers and noise. Secure transfers in the PHY layer reduce the signal processing power to perform such tasks while still meeting latency requirements.

Although chaos coding based communications for MRI coils has been described with reference to several exemplary embodiments, it is understood that the words that have been used are words of description and illustration, rather than words of limitation. Changes may be made within the purview of the appended claims, as presently stated and as amended, without departing from the scope and spirit of chaos coding based communications for MRI coils in its aspects. Although chaos coding based communications for MRI coils has been described with reference to particular means, materials and embodiments, chaos coding based communications for MRI coils is not intended to be limited to the particulars disclosed; rather chaos coding based communications for MRI coils extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

According to an aspect of the present disclosure, a method for communicating magnetic resonance imaging information wirelessly includes detecting a magnetic resonance imaging system emission sequence. The method also includes identifying at least one parameter of the magnetic resonance imaging system emission sequence. The method also may include cross-correlating the at least one parameter identified. The method may further include determining, based on the at least one parameter, a first initial condition for a first chaotic coded sequence and a second initial condition for a second chaotic coded sequence. The method may moreover include obtaining, from a modulation symbol (e.g., a QAM symbol) mapped to magnetic resonance imaging information generated at a local coil responsive to the magnetic resonance imaging system emission sequence, a real component of the symbol and an imaginary component of the symbol. The real component of the symbol is encrypted based on the first initial condition. The imaginary component of the symbol is encrypted based on the second initial condition. The encrypted real component and imaginary component of the symbol used to communicate the magnetic resonance imaging information are wirelessly transmitted.

In the method, the detecting may occur at the local coil that receives the weak radio frequency signal from the subject, but may also occur at a receiver of a communications link that is physically attached to, connected to, or otherwise integrated with the local coil. According to another aspect of the present disclosure, the encrypting is performed at a PHY layer of such a communications link dedicated to the local coil and used to wirelessly transmit the encrypted real component and imaginary component of the symbol used to communicate the magnetic resonance imaging information.

According to yet another aspect of the present disclosure, there is at least one parameter that includes a sequence of the magnetic resonance imaging emission sequence.

According to yet another aspect of the present disclosure, a first encryption key used for the encrypting the real component is composed of the first chaotic coded sequence. A second encryption key used for the encrypting the imaginary component is composed of the second chaotic coded sequence.

According to another aspect of the present disclosure, there is at least one parameter of the magnetic resonance imaging system emission sequence that includes transmission parameters.

According to yet another aspect of the present disclosure, there is at least one parameter of the magnetic resonance imaging system emission sequence that includes reception parameters of a signal received at the local coil and used to generate the magnetic resonance imaging information.

According to still another aspect of the present disclosure, the encrypting varies for each magnetic resonance imaging system emission sequence emitted by a magnetic resonance imaging system.

According to another aspect of the present disclosure, the encrypting the real component includes mapping the first initial condition through a map to produce a first encryption key sequence composed of the first chaotic coded sequence. The encrypting the imaginary component includes mapping the second initial condition through the map to produce a second encryption key sequence composed of the second chaotic coded sequence.

According to yet another aspect of the present disclosure, the encrypting the real component includes multiplying the real component by the first encryption key sequence, and the encrypting the imaginary component includes multiplying the imaginary component by the second encryption key sequence.

According to still another aspect of the present disclosure, the modulation symbol is mapped to the magnetic resonance imaging information via constellation mapping.

According to another aspect of the present disclosure, the method includes separating the real component and imaginary component of the symbol.

According to yet another aspect of the present disclosure, the first initial condition is determined as a function of a first time stamp and a first correlation factor generated from the cross-correlating. The second initial condition is determined as a function of a second time stamp and a second correlation factor generated from the cross-correlating.

According to yet another aspect of the present disclosure, the method also includes detecting that an unauthorized coil is incapable of communicating the magnetic resonance imaging data using the communications system.

According to another aspect of the present disclosure, the method includes performing error correction at the PHY layer of the communications link.

According to yet another aspect of the present disclosure, the first chaotic coded sequence and the second chaotic coded sequence are defined by the magnetic resonance imaging system such that encryption keys used for the encoding vary for each of a plurality of sessions of the magnetic resonance imaging system.

According to an aspect of the present disclosure, a communications apparatus for communicating magnetic resonance imaging information wirelessly includes a receiver, an encryption subsystem, and a transmitter. The receiver detects and receives a detected magnetic resonance imaging system emission sequence detected. The encryption subsystem identifies at least one parameter of the magnetic resonance imaging system emission sequence; cross-correlates the at least one parameter identified; determines, based on the at least one parameter, a first initial condition for a first chaotic coded sequence and a second initial condition for a second chaotic coded sequence; obtains, from a modulation symbol (e.g., a QAM symbol) mapped to magnetic resonance imaging information generated at a local coil responsive to the magnetic resonance imaging system emission sequence, a real component of the symbol and an imaginary component of the symbol; encrypts, based on the first initial condition, the real component of the symbol; and encrypts, based on the second initial condition, the imaginary component of the symbol. The transmitter wirelessly transmits the encrypted real component and imaginary component of the symbol used to communicate the magnetic resonance imaging information.

According to another aspect of the present disclosure, the encryption subsystem includes a memory and a processor. The memory stores instructions. The processor executes the instructions. When executed by the processor, the instructions cause the processor to perform operations that include the identifying at least one parameter of the magnetic resonance imaging system emission sequence, the cross-correlating the at least one parameter identified, the determining, based on the at least one parameter, the first initial condition for a first chaotic coded sequence and the second initial condition for a second chaotic coded sequence, the encrypting, based on the first initial condition, the real component of the symbol used to communicate magnetic resonance imaging information, and the encrypting, based on the second initial condition, the imaginary component of the symbol used to communicate the magnetic resonance imaging information, According to yet another aspect of the present disclosure, the encrypting by the encryption subsystem is performed at a PHY layer of the communications apparatus, and the communications apparatus is dedicated to the local coil and used to wirelessly transmit the encrypted real component and imaginary component of the symbol used to communicate the magnetic resonance imaging information.

According to yet another aspect of the present disclosure, error correction is performed at the PHY layer of the communications apparatus.

According to an aspect of the present disclosure, a tangible non-transitory computer readable storage medium stores a computer program. The computer program, when executed by a processor, causes a communications apparatus for communicating magnetic resonance imaging information wirelessly to perform a process. The process includes detecting a magnetic resonance imaging system emission sequence, and identifying at least one parameter of the magnetic resonance imaging system emission sequence. The process also includes cross-correlating the at least one parameter identified, and determining, based on the at least one parameter, a first initial condition for a first chaotic coded sequence and a second initial condition for a second chaotic coded sequence. The process may moreover include obtaining, from a modulation symbol (e.g., a QAM symbol) mapped to magnetic resonance imaging information generated at a local coil responsive to the magnetic resonance imaging system emission sequence, a real component of the symbol and an imaginary component of the symbol. A real component of a symbol used to communicate magnetic resonance imaging information is encrypted based on the first initial condition. An imaginary component of the symbol used to communicate the magnetic resonance imaging information is encrypted based on the second initial condition. The encrypted real component and imaginary component of the symbol used to communicate the magnetic resonance imaging information are wirelessly transmitted.

As described above, a secure system can also meet delay (latency) requirements. Using the system and methods described herein, use of unauthorized coils can be detected and prevented, and MRI data can be protected from hackers as well as from noisy environments that might otherwise lead to corruption of data.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A method for communicating magnetic resonance imaging (MRI) information wirelessly, comprising:
   detecting a magnetic resonance imaging system emission sequence;
   identifying at least one parameter of the magnetic resonance imaging system emission sequence;
   cross-correlating the at least one parameter identified;
   determining, based on the at least one parameter, a first initial condition for a first chaotic coded sequence and a second initial condition for a second chaotic coded sequence;
   obtaining, from a modulation symbol mapped to magnetic resonance imaging information generated at a local coil responsive to the magnetic resonance imaging system emission sequence, a real component of the modulation symbol and an imaginary component of the modulation symbol;
   encrypting, based on the first initial condition, the real component of the modulation symbol to produce an encrypted real component;
   encrypting, based on the second initial condition, the imaginary component of the modulation symbol to produce an encrypted imaginary component; and wirelessly transmitting the encrypted real component and the encrypted imaginary component of the modulation symbol used to communicate the magnetic resonance imaging information.

2. The method of claim 1,
wherein the encrypting is performed at a PHY layer of a communications link dedicated to the local coil and used to wirelessly transmit the encrypted real component and the encrypted imaginary component of the modulation symbol used to communicate the magnetic resonance imaging information.

3. The method of claim 1,
wherein the at least one parameter comprises a sequence of the magnetic resonance imaging emission sequence.

4. The method of claim 1,
wherein an encryption key used for the encrypting the real component is composed of the first chaotic coded sequence, and
an encryption key used for the encrypting the imaginary component is composed of the second chaotic coded sequence.

5. The method of claim 4,
wherein the at least one parameter of the magnetic resonance imaging system emission sequence comprises transmission parameters.

6. The method of claim 4,
wherein the at least one parameter of the magnetic resonance imaging system emission sequence comprises reception parameters of a signal received at the local coil.

7. The method of claim 1,
wherein the encrypting varies for each magnetic resonance imaging system emission sequence emitted by a magnetic resonance imaging system.

8. The method of claim 1,
wherein the encrypting the real component comprises mapping the first initial condition through a map to produce a first encryption key sequence composed of the first chaotic coded sequence, and
wherein the encrypting the imaginary component comprises mapping the second initial condition through the map to produce a second encryption key sequence composed of the second chaotic coded sequence.

9. The method of claim 8,
wherein the encrypting the real component comprises multiplying the real component by the first encryption key sequence, and the encrypting the imaginary component comprises multiplying the imaginary component by the second encryption key sequence.

10. The method of claim 1,
wherein a quadrature amplitude modulation symbol is mapped to the magnetic resonance imaging information via constellation mapping.

11. The method of claim 1, further comprising:
separating the real component and imaginary component of the modulation symbol.

12. The method of claim 1,
wherein the first initial condition is determined as a function of a first time stamp and a first correlation factor generated from the cross-correlating, and
the second initial condition is determined as a function of a second time stamp and a second correlation factor generated from the cross-correlating.

13. The method of claim 12, further comprising:
detecting that an unauthorized coil is incapable of communicating magnetic resonance imaging data using a communications system.

14. The method of claim 2, further comprising:
performing error correction at the PHY layer of the communications link.

15. The method of claim 1,
wherein the first chaotic coded sequence and the second chaotic coded sequence are defined by a magnetic resonance imaging system such that encryption keys used for encoding vary for each of a plurality of sessions of the magnetic resonance imaging system.

16. A communications apparatus for communicating magnetic resonance imaging (MRI) information wirelessly, comprising:
a receiver that detects and receives a magnetic resonance imaging system emission sequence;
an encryption subsystem that identifies at least one parameter of the magnetic resonance imaging system emission sequence; that cross-correlates the at least one parameter identified; that determines, based on the at least one parameter, a first initial condition for a first chaotic coded sequence and a second initial condition for a second chaotic coded sequence; that obtains, from a modulation symbol mapped to magnetic resonance imaging information generated at a local coil responsive to the magnetic resonance imaging system emission sequence, a real component of the modulation symbol and an imaginary component of the modulation symbol; that encrypts, based on the first initial condition, the real component of the modulation symbol to produce an encrypted real component; and that encrypts, based on the second initial condition, the imaginary component of the modulation symbol to produce an encrypted imaginary component, and
a transmitter that wirelessly transmits the encrypted real component and the encrypted imaginary component of the modulation symbol used to communicate the magnetic resonance imaging information.

17. The communications apparatus of claim 16, wherein the encryption subsystem comprises:
a memory that stores instructions, and
a processor that executes the instructions,
wherein, when executed by the processor, the instructions cause the processor to perform operations comprising:
the identifying at least one parameter of the magnetic resonance imaging system emission sequence;
the cross-correlating the at least one parameter identified;
the determining, based on the at least one parameter, the first initial condition for a first chaotic coded sequence and the second initial condition for a second chaotic coded sequence;
the encrypting, based on the first initial condition, the real component of the modulation symbol used to communicate magnetic resonance imaging information; and
the encrypting, based on the second initial condition, the imaginary component of the modulation symbol used to communicate the magnetic resonance imaging information.

18. The communications apparatus of claim 16,
wherein the encrypting by the encryption subsystem is performed at a PHY layer of the communications apparatus, and
the communications apparatus is dedicated to the local coil and used to wirelessly transmit the encrypted real component and imaginary component of the modulation symbol used to communicate the magnetic resonance imaging information.

19. The communications apparatus of claim 18,
wherein error correction is performed at the PHY layer of the communications apparatus.

20. A tangible non-transitory computer readable storage medium that stores a computer program, the computer program, when executed by a processor, causing a communications apparatus for communicating magnetic resonance imaging (MRI) information wirelessly to perform a process comprising:
  detecting a magnetic resonance imaging system emission sequence;
  identifying at least one parameter of the magnetic resonance imaging system emission sequence;
  cross-correlating the at least one parameter identified;
  determining, based on the at least one parameter, a first initial condition for a first chaotic coded sequence and a second initial condition for a second chaotic coded sequence;
  obtaining, from a modulation symbol mapped to magnetic resonance imaging information generated at a local coil responsive to the magnetic resonance imaging system emission sequence, a real component of the modulation symbol and an imaginary component of the modulation symbol;
  encrypting, based on the first initial condition, the real component of the modulation symbol to produce an encrypted real component;
  encrypting, based on the second initial condition, the imaginary component of the modulation symbol to produce an encrypted imaginary component; and
  wirelessly transmitting the encrypted real component and the encrypted imaginary component of the modulation symbol used to communicate the magnetic resonance imaging information.

\* \* \* \* \*